United States Patent [19]

Ozaki et al.

[11] 4,032,524
[45] June 28, 1977

[54] 1-CARBAMOYL-5-FLUOROURACIL DERIVATIVES

[75] Inventors: Shoichiro Ozaki, Kamakura; Haruki Mori, Yokohama, both of Japan

[73] Assignee: Mitsui Toatsu Chemicals, Incorporated, Tokyo, Japan

[22] Filed: Sept. 24, 1976

[21] Appl. No.: 726,196

Related U.S. Application Data

[63] Continuation-in-part of Ser. No. 555,445, March 5, 1975, abandoned.

[30] Foreign Application Priority Data

Apr. 26, 1974   Japan .............................. 49-46617

[52] U.S. Cl. ........................ 260/256.4 C; 424/251
[51] Int. Cl.² ...................................... C07D 239/10
[58] Field of Search ........................... 260/256.4 C

[56] References Cited

OTHER PUBLICATIONS

Ozaki, et al.; "Chemical Abstracts", vol. 82, 1975, col. 171016g.
Ozaki, et al.; "Chemical Abstracts", vol. 82, 1975, col. 140297v.

"Doklady Akademii Nauk SSSR", vol. 176 (2), 1967, pp. 332-335.

*Primary Examiner*—Donald G. Daus
*Assistant Examiner*—James H. Turnipseed
*Attorney, Agent, or Firm*—Fisher, Christen & Sabol

[57] ABSTRACT

1-Carbamoyl-5-fluorouracil derivatives represented by the formula

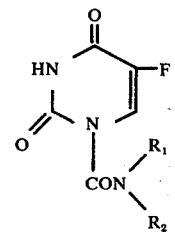

wherein $R_1$ represents methyl, ethyl, phenyl or cyclohexyl and $R_2$ represents hydrogen or is the same as $R_1$ are effective anti-metabolites useful in treating lymphatic leukemia L1210, sarcoma 180A and Ehrlich ascites carcinoma in mice.

6 Claims, No Drawings

1-CARBAMOYL-5-FLUOROURACIL DERIVATIVES

CROSS-REFERENCE TO RELATED APPLICATION

This application is a continuation-in-part of application Ser. No. 555,445 filed Mar. 5, 1975, now abandoned.

BACKGROUND OF THE INVENTION

1. Field of the Invention

The present invention relates to 5-fluorouracil derivatives and, more particularly, to novel 1-carbamoyl-5-fluorouracils represented by the formula

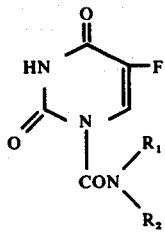

wherein $R_1$ represents methyl, ethyl, phenyl or cyclohexyl and $R_2$ represents hydrogen or is the same as $R_1$.

2. Description of the Prior Art

5-Fluorouracil is well known to be an effective anti-metabolite used as an anti-tumor agent. However, due to its high toxicity, 5-fluorouracil is not considered to be a favorable anti-tumor agent and improvement has been recognized as necessary. On the other hand, as a low toxic 5-fluorouracil derivative, there is known 5-fluoro-1-(2-tetrahydrofuryl)uracil which has been used as an anti-tumor agent. However, this compound is substantially inferior to 5-fluorouracil in anti-tumor activity and it has been desired to develop 5-fluorouracil derivatives which are as non-toxic as 5-fluoro-1-(2-tetrahydrofuryl)uracil and are also substantially more effective anti-metabolites.

SUMMARY OF THE INVENTION

The 1-carbamoyl-5-fluorouracils of the present invention are more effective anti-metabolites than 5-fluoro-1-(2-tetrahydrofuryl)uracil and are as low in toxicity as that prior art compound. The 1-carbamoyl-5-fluorouracils of the present invention are prepared by carbamolyating 5-fluorouracil with an isocyanate or carbamoyl halide.

DESCRIPTION OF THE PREFERRED EMBODIMENTS

In the 1-carbamoyl-5-fluorouracils of the present invention, $R_1$ may represent methyl, ethyl, phenyl or cyclohexyl and $R_2$ may represent hydrogen or be the same as $R_1$. The compounds are prepared by carbamolyating 5-fluorouracil with an isocyanate having the formula

$$R_1-NCO$$

or a carbamoyl halide having the formula

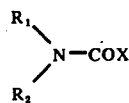

wherein $R_1$ and $R_2$ are as defined above and X is halogen.

Suitable isocyanates for use in the reaction include methyl isocyanate, phenyl isocyanate, cyclohexyl isocyanate and ethyl isocyanate.

Suitable carbamoyl halides for use in the reaction include N,N-diethylcarbamoyl chloride, N,N-dimethylcarbamoyl chloride and the corresponding bromides.

The reaction is ordinarily carried out in an organic solvent. Organic solvents such as dimethyl sulfoxide, dimethylformamide, dimethyl acetamide, acetonitrile, and the like are suitable for this purpose. 5-Fluorouracil is dissolved in the organic solvent, one of the above isocyanates or carbamoyl halides is added thereto and the reaction mixture is stirred at a temperature ranging from room temperature to the reflux temperature of the reaction mixture. When a carbamoyl halide is employed, the reaction is preferably carried out in the presence of an acid acceptor of the hydrogen halide formed during the reaction. Such acid acceptors include, for example, triethylamine, pyridine, potassium carbonate, sodium bicarbonate, sodium hydride, and the like.

The reaction mixture is preferably filtered off or concentrated under reduced pressure and the obtained crude product is purified, e.g., by washing, recrystallization, and like methods. The 1-carbamoyl-5-fluorouracils thus obtained are white needles, leaflets or granules and are excellent anti-metabolites useful in treating lymphatic leukemia L1210, sarcoma 180A and Ehrlich ascites carcinoma in mice.

The following examples illustrate methods for preparing the 1-carbamoyl-5-fluorouracils of the present invention.

EXAMPLE 1

10.4 g. (0.08 mole) of 5-fluorouracil was dissolved in 100 ml. of dimethyl sulfoxide, then 14.3 g. (0.12 mole) of phenyl isocyanate was added thereto and stirred at room temperature for 1 hour. The milky reaction mixture was filtered off and a fine precipitate was obtained. The precipitate was suspended in hot ethanol and again filtered. There was obtained 16.2 g. (81.4% yield) of 5-fluoro-1-phenyl carbamoyluracil melting at 280° C.

Results of an elementary analysis thereof were well in agreement with the calculated values as follows:

|  | C | H | F | N |
|---|---|---|---|---|
| Found (%) | 52.83 | 3.19 | 7.64 | 16.43 |
| Calcd. (%) | 53.02 | 3.24 | 7.63 | 16.86 |
| (for $C_{11}H_8FN_3O_3$) | | | | |

EXAMPLE 2

10.4 g. (0.08 mole) of 5-fluorouracil and 10.0 g. (0.176 mole) of methyl isocyanate were mixed in 100 ml. of dimethyl sulfoxide and stirred at room temperature. Dimethyl sulfoxide and excess methyl isocyanate were removed from the reaction mixture by distillation. The resultant residue was washed with chloroform and dried in a vacuum oven to give 15.8 g. (86.1% yield) of 5-fluoro-1-methylcarbamoyluracil. The product was recrystallized from ethyl acetate and there were obtained white crystals melting at 277° C.

Results of an elementary analysis of the above product were well in agreement with the calculated values as follows:

|  | C | H | F | N |
|---|---|---|---|---|
| Found (%) | 38.23 | 3.22 | 10.10 | 22.31 |
| Calcd. (%) | 38.51 | 3.23 | 10.15 | 22.46 |
|  | (for $C_6H_6FN_3O_3$) | | | |

EXAMPLE 3

The method of Example 2 was repeated with the exception that cyclohexyl isocyanate was used instead of methyl isocyanate. 1-Cyclohexylcarbamoyl-5-fluorouracil melting at 276°–278° C. was obtained.

EXAMPLE 4

1.3 g. (0.01 mole) of 5-fluorouracil was dissolved in 20 ml. of dimethyl acetamide and then 0.48 g. (0.01 mole) of 50% sodium hydride was added thereto. Subsequently, 1.36 g. (0.01 mole) of N,N-diethylcarbamoyl chloride in 5 ml. of dimethyl acetamide was added dropwise at 30° C. After stirring at 30° C. for 5 hours, the reaction mixture was allowed to stand overnight at room temperature. The reaction mixture was filtered and the resultant filtrate was evaporated under reduced pressure. The residue obtained was extracted with 30 ml. of chloroform and the extract was concentrated to dryness to give 2.14 g. of crude product. The product was washed with diethyl ether and 1.73 g. (75.5% yield) of 1-(N,N-diethylcarbamoyl)-5-fluorouracil melting at 157°–160° C. was obtained.

Results of an elementary analysis of this product were well in agreement with the calculated values as follows:

|  | C | H | F | N |
|---|---|---|---|---|
| Found (%) | 47.23 | 5.27 | 8.11 | 18.09 |
| Calcd. (%) | 47.16 | 5.28 | 8.29 | 18.33 |
|  | (for $C_9H_{12}FN_3O_3$) | | | |

EXAMPLE 5

The method of Example 4 was repeated with the exception that N,N-dimethylcarbamoyl chloride was used instead of N,N-diethylcarbamoyl chloride. 1-(N,N-dimethylcarbamoyl)-5-fluorouracil melting at 194°–196° C. was obtained.

The anti-tumor activities of the 1-carbamoyl-5-fluorouracils of the present invention were measured according to the procedure set forth below, and compared with that of well known 5-fluoro-1-(2-tetrahydrofuryl)uracil.

PROCEDURE FOR THE MEASUREMENT OF ANTI-TUMOR ACTIVITY $BDF_1$ mice weighing 18–20 g. and caused to have lymphatic leukemia (L1210) were used for this purpose. Each test compound and 5-fluoro-1-(2-tetrahydrofuryl)uracil as a standard was individually administered intraperitoneally to the mice at a daily dose of 30 mg./kg. for 5 days and the percent Increased Life Span (ILS%) was observed for each mouse.

The results of the above-described anti-tumor activity measurements made according to the above procedure are summarized below in Table 1.

Table 1

| Compound | ILS (%) |
|---|---|
| 5-fluoro-1-(2-tetrahydrofuryl)uracil | 100 |
| 5-fluoro-1-phenylcarbamoyluracil | 148 |
| 5-fluoro-1-methylcarbamoyluracil | 150 |
| 1-cyclohexylcarbamoyl-5-fluorouracil | 116 |
| 1-(N,N-diethylcarbamoyl)-5-fluorouracil | 104 |
| 1-(N,N-dimethylcarbamoyl)-5-fluorouracil | 129 |

In addition to the above anti-tumor activity, 5-fluoro-1-methylcarbamoyluracil of the present invention has an inhibiting effect on sarcoma 180A three times as potent as that of 5-fluoro-1-(2-tetrahydrofuryl)uracil (FT-207) and an inhibiting effect on Ehrlich ascites carcinoma two times as potent as that of FT-207. 1-Cyclohexylcarbamoyl-5-fluorouracil has also an inhibiting effect on sarcoma 180A two times as potent as that of FT-207 and an inhibiting effect on Ehrlich ascites carcinoma equal to that of FT-207.

The 1-carbamoyl-5-fluorouracils of the present invention are less toxic than FT-207. The medial lethal doses ($LD_{50}$) of the claimed compounds for mice are 1000–1200 mg./kg. and the minimum effective dose of the same compounds for lymphatic leukemia L1210 in mice is 15–50 mg./kg.

The above data are concerned with mice and, when administering to humans, a daily dosage unit of the claimed compounds comprises from 1 to 20 mg./kg. A preferred dosage unit form is a capsule containing 100–300 mg. of a claimed compound as the therapeutically active ingredient and 200–700 mg. of carrier vehicles such as lactose, corn starch, and the like. The capsule may be of either the hard or soft variety and may be made of any suitable capsule material which will disintegrate in the digestive tract in from about 1 to 4 hours. Examples of such encapsulating materials are gelatin and methyl cellulose.

The claimed compounds may be administered either orally or intravenously.

What is claimed is:

1. A 1-carbamoyl-5-fluorouracil represented by the formula

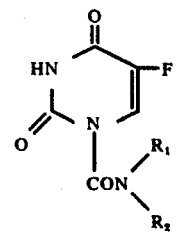

wherein $R_1$ represents methyl, ethyl, phenyl or cyclohexyl and $R_2$ represents hydrogen or is the same as $R_1$.

2. The 1-carbamoyl-5-fluorouracil of claim 1 wherein $R_1$ is phenyl, $R_2$ is hydrogen and the compund is 5-fluoro-1-phenylcarbamoyluracil.

3. The 1-carbamoyl-5-fluorouracil of claim 1 wherein $R_1$ is methyl, $R_2$ is hydrogen and the compound is 5-fluoro-1-methylcarbamoyluracil.

4. The 1-carbamoyl-5-fluorouracil of claim 1 wherein $R_1$ is cyclohexyl, $R_2$ is hydrogen and the compound is 1-cyclohexylcarbamoyl-5-fluorouracil.

5. The 1-carbamoyl-5-fluorouracil of claim 1 wherein $R_1$ and $R_2$ are each ethyl and the compound is 1-(N,N-diethylcarbamoyl)-5-fluorouracil.

6. The 1-carbamoyl-5-fluorouracil of claim 1 wherein $R_1$ and $R_2$ are each ethyl and the compound is 1-(N,N-dimethylcarbamoyl)-5-fluorouracil.

* * * * *